(12) United States Patent
Lin et al.

(10) Patent No.: US 10,918,681 B2
(45) Date of Patent: Feb. 16, 2021

(54) METHOD FOR REGULATING EXPRESSION OF PDGFC, FGF2, IGF1R, PTGIS, NOS3, EDN1, PLAT, PROC, VWF, F3, SERPINE1, IL-8, ICAM1, VCAM1, AND CASP8 GENES

(71) Applicant: TCI CO., LTD., Taipei (TW)

(72) Inventors: Yung-Hsiang Lin, Taipei (TW); I-Hui Chen, Taipei (TW); Kai-Wen Kan, Taipei (TW); Fu Chen Liu, Taipei (TW); Ciao-Ting Chen, Taipei (TW)

(73) Assignee: TCI CO., LTD., Taipei (TW)

( * ) Notice: Subject to any disclaimer, the term of this patent is extended or adjusted under 35 U.S.C. 154(b) by 14 days.

(21) Appl. No.: 16/498,737

(22) PCT Filed: Apr. 3, 2018

(86) PCT No.: PCT/CN2018/081719
§ 371 (c)(1),
(2) Date: Sep. 27, 2019

(87) PCT Pub. No.: WO2018/184526
PCT Pub. Date: Oct. 11, 2018

(65) Prior Publication Data
US 2020/0368306 A1    Nov. 26, 2020

Related U.S. Application Data

(60) Provisional application No. 62/503,185, filed on May 8, 2017, provisional application No. 62/480,860, filed on Apr. 3, 2017.

(51) Int. Cl.
| | | |
|---|---|---|
| *A61K 36/00* | (2006.01) |
| *A61K 36/185* | (2006.01) |
| *A23L 33/105* | (2016.01) |
| *A61K 9/00* | (2006.01) |
| *A61K 9/08* | (2006.01) |
| *A61K 9/48* | (2006.01) |
| *A61P 3/04* | (2006.01) |
| *A61K 31/01* | (2006.01) |
| *A61K 31/015* | (2006.01) |
| *A61K 36/21* | (2006.01) |
| *A61K 36/258* | (2006.01) |
| *A61K 36/31* | (2006.01) |
| *A61K 36/45* | (2006.01) |
| *A61K 36/48* | (2006.01) |
| *A61K 36/53* | (2006.01) |
| *A61K 36/67* | (2006.01) |
| *A61K 36/73* | (2006.01) |
| *A61K 36/74* | (2006.01) |
| *A61K 36/752* | (2006.01) |
| *A61K 36/815* | (2006.01) |
| *A61K 36/82* | (2006.01) |
| *A61K 36/87* | (2006.01) |
| *A61K 36/886* | (2006.01) |
| *A61K 36/8962* | (2006.01) |
| *A61K 36/9066* | (2006.01) |
| *A61K 8/9789* | (2017.01) |
| *A61P 17/16* | (2006.01) |
| *A61Q 19/00* | (2006.01) |
| *A23F 3/16* | (2006.01) |
| *A61K 8/97* | (2017.01) |
| *A61Q 17/04* | (2006.01) |

(Continued)

(52) U.S. Cl.
CPC ............ *A61K 36/185* (2013.01); *A23F 3/163* (2013.01); *A23L 33/105* (2016.08); *A61K 8/97* (2013.01); *A61K 8/9789* (2017.08); *A61K 9/0056* (2013.01); *A61K 9/0095* (2013.01); *A61K 9/08* (2013.01); *A61K 9/48* (2013.01); *A61K 31/01* (2013.01); *A61K 31/015* (2013.01); *A61K 36/21* (2013.01); *A61K 36/258* (2013.01); *A61K 36/31* (2013.01); *A61K 36/45* (2013.01); *A61K 36/48* (2013.01); *A61K 36/53* (2013.01); *A61K 36/67* (2013.01); *A61K 36/73* (2013.01); *A61K 36/74* (2013.01); *A61K 36/752* (2013.01); *A61K 36/815* (2013.01); *A61K 36/82* (2013.01); *A61K 36/87* (2013.01); *A61K 36/886* (2013.01); *A61K 36/8962* (2013.01); *A61K 36/9066* (2013.01); *A61P 3/04* (2018.01); *A61P 17/16* (2018.01); *A61P 19/04* (2018.01); *A61Q 17/04* (2013.01); *A61Q 19/007* (2013.01); *A61Q 19/08* (2013.01); *A23V 2002/00* (2013.01)

(58) Field of Classification Search
CPC ..................................................... A61K 36/00
USPC ....................................................... 424/725
See application file for complete search history.

(56) References Cited

FOREIGN PATENT DOCUMENTS

| CN | 101317615 A | 12/2008 |
| CN | 102524782 A | 7/2012 |

OTHER PUBLICATIONS

Zhao, Guoling et al., "A Review on Phenolic Compounds from Edible Plants and their Protective Activities in Vivo Through Antioxidation", p. 40-45, Dec. 31, 2009, Biotechnology Bulletin, China.

*Primary Examiner* — Michael V Meller
(74) *Attorney, Agent, or Firm* — Chieh-Mei Wang

(57) ABSTRACT

The present disclosure provides a method for regulating expression of PDGFC, FGF2, IGF1R, PTGIS, NOS3, EDN1, PLAT, PROC, VWF, F3, SERPINE1, IL-8, ICAM1, VCAM1, and CASP8 genes, including administering to a subject in need thereof a composition including an effective amount of a plant extract, wherein the plant extract includes at least one combination selected from the group consisting of a grape seed extract and a Four seasons spring tea extract, a black tea extract and a spinach extract, the grape seed extract and the spinach extract, the grape seed extract and a (Continued)

green coffee bean extract, a red wine extract and a Pu-erh tea extract, and the grape seed extract and the Pu-erh tea extract.

4 Claims, 1 Drawing Sheet

Specification includes a Sequence Listing.

(51) Int. Cl.
*A61P 19/04* (2006.01)
*A61Q 19/08* (2006.01)

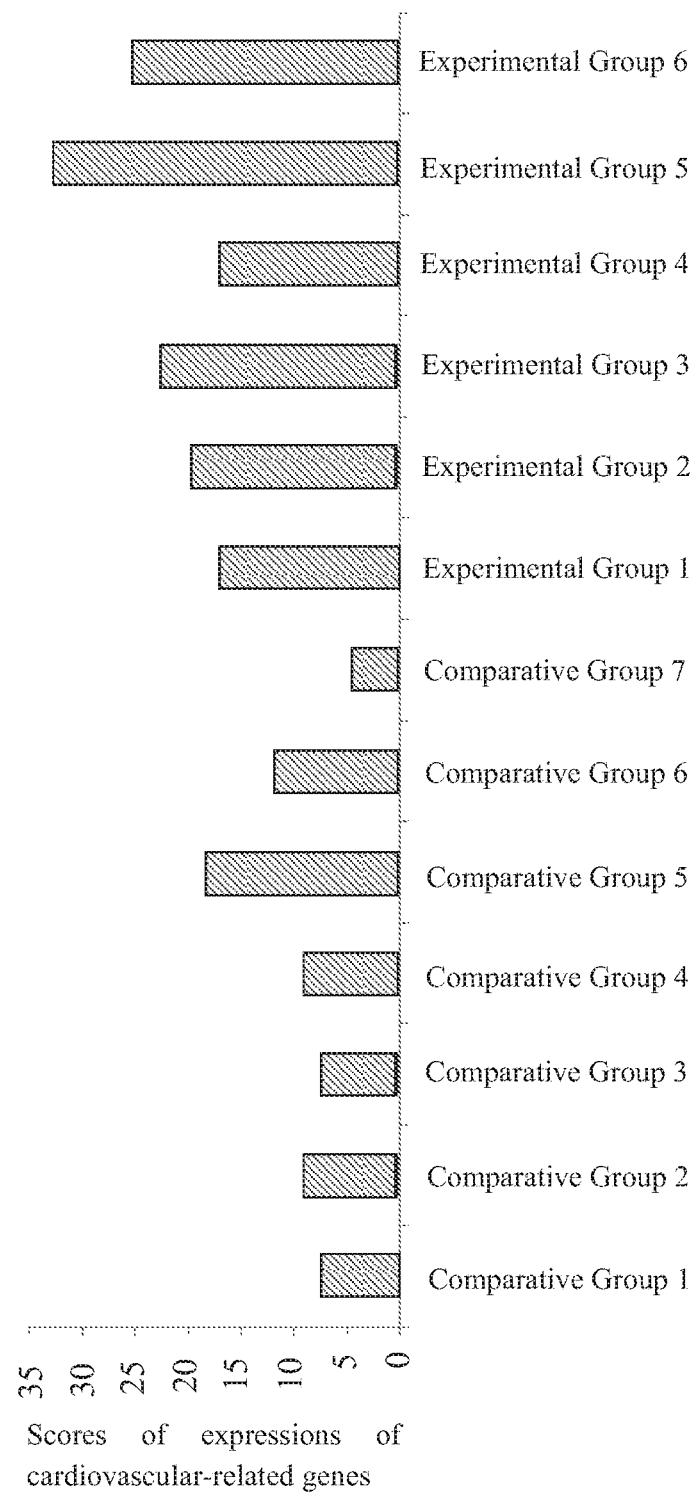

SEQUENCE LISTING

<160> NUMBER OF SEQ ID NOS: 32

<210> SEQ ID NO 1
<211> LENGTH: 17
<212> TYPE: DNA
<213> ORGANISM: Artificial Sequence
<220> FEATURE:
<223> OTHER INFORMATION: forward primer for PCR

<400> SEQUENCE: 1
ggcagacggg cgagaat                                                17

<210> SEQ ID NO 2
<211> LENGTH: 16
<212> TYPE: DNA
<213> ORGANISM: Artificial Sequence
<220> FEATURE:
<223> OTHER INFORMATION: reverse primer for PCR

<400> SEQUENCE: 2 cccccccaggg catgtt                                                16

<210> SEQ ID NO 3
<211> LENGTH: 24
<212> TYPE: DNA
<213> ORGANISM: Artificial Sequence
<220> FEATURE:
<223> OTHER INFORMATION: forward primer for PCR

<400> SEQUENCE: 3
gttcacctac atctgcaacc acat                                        24

<210> SEQ ID NO 4
<211> LENGTH: 21
<212> TYPE: DNA
<213> ORGANISM: Artificial Sequence
<220> FEATURE:
<223> OTHER INFORMATION: reverse primer for PCR

<400> SEQUENCE: 4
aatgcagagc tcggtgatct c                                           21

<210> SEQ ID NO 5
<211> LENGTH: 22
<212> TYPE: DNA
<213> ORGANISM: Artificial Sequence
<220> FEATURE:
<223> OTHER INFORMATION: forward primer for PCR

<400> SEQUENCE: 5
cacgttgttc cgtatggact tg                                          22

<210> SEQ ID NO 6
<211> LENGTH: 29
<212> TYPE: DNA
<213> ORGANISM: Artificial Sequence
<220> FEATURE:
<223> OTHER INFORMATION: reverse primer for PCR

<400> SEQUENCE: 6
cctttcttat gattattcca gtctttctc                                   29

<210> SEQ ID NO 7
<211> LENGTH: 20
<212> TYPE: DNA
<213> ORGANISM: Artificial Sequence

```
<220> FEATURE:
<223> OTHER INFORMATION: forward primer for PCR

<400> SEQUENCE: 7
cagcctcagt ttcgcatcaa                                              20

<210> SEQ ID NO 8
<211> LENGTH: 21
<212> TYPE: DNA
<213> ORGANISM: Artificial Sequence
<220> FEATURE:
<223> OTHER INFORMATION: reverse primer for PCR

<400> SEQUENCE: 8
cggtatgttc tgcccaagat c                                            21

<210> SEQ ID NO 9
<211> LENGTH: 24
<212> TYPE: DNA
<213> ORGANISM: Artificial Sequence
<220> FEATURE:
<223> OTHER INFORMATION: forward primer for PCR

<400> SEQUENCE: 9
ttcaatcacc ttggtcacat cttc                                         24

<210> SEQ ID NO 10
<211> LENGTH: 19
<212> TYPE: DNA
<213> ORGANISM: Artificial Sequence
<220> FEATURE:
<223> OTHER INFORMATION: reverse primer for PCR

<400> SEQUENCE: 10
cgctgcacag tccattcct                                               19

<210> SEQ ID NO 11
<211> LENGTH: 20
<212> TYPE: DNA
<213> ORGANISM: Artificial Sequence
<220> FEATURE:
<223> OTHER INFORMATION: forward primer for PCR

<400> SEQUENCE: 11
cgtacttggc acgggtcttc                                              20

<210> SEQ ID NO 12
<211> LENGTH: 25
<212> TYPE: DNA
<213> ORGANISM: Artificial Sequence
<220> FEATURE:
<223> OTHER INFORMATION: reverse primer for PCR

<400> SEQUENCE: 12
ccttctgact aaagtccgtt catct                                        25

<210> SEQ ID NO 13
<211> LENGTH: 23
<212> TYPE: DNA
<213> ORGANISM: Artificial Sequence
<220> FEATURE:
<223> OTHER INFORMATION: forward primer for PCR

<400> SEQUENCE: 13
gtggagagag ccagattcat cat                                          23
```

<210> SEQ ID NO 14
<211> LENGTH: 20
<212> TYPE: DNA
<213> ORGANISM: Artificial Sequence
<220> FEATURE:
<223> OTHER INFORMATION: reverse primer for PCR

<400> SEQUENCE: 14
ctgccgtctg atttgtggaa                                                    20

<210> SEQ ID NO 15
<211> LENGTH: 21
<212> TYPE: DNA
<213> ORGANISM: Artificial Sequence
<220> FEATURE:
<223> OTHER INFORMATION: forward primer for PCR

<400> SEQUENCE: 15
ggagcttcgt gtcctgtatg g                                                  21

<210> SEQ ID NO 16
<211> LENGTH: 20
<212> TYPE: DNA
<213> ORGANISM: Artificial Sequence
<220> FEATURE:
<223> OTHER INFORMATION: reverse primer for PCR

<400> SEQUENCE: 16
agcctggcac attggagtct                                                    20

<210> SEQ ID NO 17
<211> LENGTH: 23
<212> TYPE: DNA
<213> ORGANISM: Artificial Sequence
<220> FEATURE:
<223> OTHER INFORMATION: forward primer for PCR

<400> SEQUENCE: 17
gttgaaggat gcgggagtat atg                                                23

<210> SEQ ID NO 18
<211> LENGTH: 21
<212> TYPE: DNA
<213> ORGANISM: Artificial Sequence
<220> FEATURE:
<223> OTHER INFORMATION: reverse primer for PCR

<400> SEQUENCE: 18
tcatgttggc ttttcttgca a                                                  21

<210> SEQ ID NO 19
<211> LENGTH: 22
<212> TYPE: DNA
<213> ORGANISM: Artificial Sequence
<220> FEATURE:
<223> OTHER INFORMATION: forward primer for PCR

<400> SEQUENCE: 19
ttttgccaag gagtgctaaa ga                                                 22

<210> SEQ ID NO 20
<211> LENGTH: 21
<212> TYPE: DNA
<213> ORGANISM: Artificial Sequence
<220> FEATURE:
<223> OTHER INFORMATION: reverse primer for PCR

```
<400> SEQUENCE: 20
aaccctctgc acccagtttt c                                           21

<210> SEQ ID NO 21
<211> LENGTH: 20
<212> TYPE: DNA
<213> ORGANISM: Artificial Sequence
<220> FEATURE:
<223> OTHER INFORMATION: forward primer for PCR

<400> SEQUENCE: 21
tccaaatgca aactggatga                                             20

<210> SEQ ID NO 22
<211> LENGTH: 20
<212> TYPE: DNA
<213> ORGANISM: Artificial Sequence
<220> FEATURE:
<223> OTHER INFORMATION: reverse primer for PCR

<400> SEQUENCE: 22
gggcacagac tcttttcagg                                             20

<210> SEQ ID NO 23
<211> LENGTH: 18
<212> TYPE: DNA
<213> ORGANISM: Artificial Sequence
<220> FEATURE:
<223> OTHER INFORMATION: forward primer for PCR

<400> SEQUENCE: 23
tagggcgctg gtgtggtt                                               18

<210> SEQ ID NO 24
<211> LENGTH: 20
<212> TYPE: DNA
<213> ORGANISM: Artificial Sequence
<220> FEATURE:
<223> OTHER INFORMATION: reverse primer for PCR

<400> SEQUENCE: 24
aagcaggtcc agtggcaaag                                             20

<210> SEQ ID NO 25
<211> LENGTH: 23
<212> TYPE: DNA
<213> ORGANISM: Artificial Sequence
<220> FEATURE:
<223> OTHER INFORMATION: forward primer for PCR

<400> SEQUENCE: 25
tgtgctaacc gttacctggc tat                                         23

<210> SEQ ID NO 26
<211> LENGTH: 20
<212> TYPE: DNA
<213> ORGANISM: Artificial Sequence
<220> FEATURE:
<223> OTHER INFORMATION: reverse primer for PCR

<400> SEQUENCE: 26
ttctgcccag gtcctgtttt                                             20

<210> SEQ ID NO 27
```

```
<211> LENGTH: 20
<212> TYPE: DNA
<213> ORGANISM: Artificial Sequence
<220> FEATURE:
<223> OTHER INFORMATION: forward primer for PCR

<400> SEQUENCE: 27
aggaggcaaa acggtgaatg                                                    20

<210> SEQ ID NO 28
<211> LENGTH: 22
<212> TYPE: DNA
<213> ORGANISM: Artificial Sequence
<220> FEATURE:
<223> OTHER INFORMATION: reverse primer for PCR

<400> SEQUENCE: 28
cactttgcag agccttctgt tg                                                 22

<210> SEQ ID NO 29
<211> LENGTH: 22
<212> TYPE: DNA
<213> ORGANISM: Artificial Sequence
<220> FEATURE:
<223> OTHER INFORMATION: forward primer for PCR

<400> SEQUENCE: 29
gaaaggaagc ggagagatgt ca                                                 22

<210> SEQ ID NO 30
<211> LENGTH: 21
<212> TYPE: DNA
<213> ORGANISM: Artificial Sequence
<220> FEATURE:
<223> OTHER INFORMATION: reverse primer for PCR

<400> SEQUENCE: 30
tcgatgcggt acaatgtgaa a                                                  21

<210> SEQ ID NO 31
<211> LENGTH: 21
<212> TYPE: DNA
<213> ORGANISM: Artificial Sequence
<220> FEATURE:
<223> OTHER INFORMATION: forward primer for PCR

<400> SEQUENCE: 31
catgtacgtt gctatccagg c                                                  21

<210> SEQ ID NO 32
<211> LENGTH: 21
<212> TYPE: DNA
<213> ORGANISM: Artificial Sequence
<220> FEATURE:
<223> OTHER INFORMATION: reverse primer for PCR

<400> SEQUENCE: 32
ctccttaatg tcacgcacga t                                                  21
```

METHOD FOR REGULATING EXPRESSION OF PDGFC, FGF2, IGF1R, PTGIS, NOS3, EDN1, PLAT, PROC, VWF, F3, SERPINE1, IL-8, ICAM1, VCAM1, AND CASP8 GENES

CROSS-REFERENCE TO RELATED APPLICATION

This application claims priority of U.S. patent application No. 62/480,860, filed on Apr. 3, 2017, and U.S. patent application No. 62/503,185, filed on May 8, 2017, the content of which is incorporated herein in its entirety by reference.

BACKGROUND OF THE INVENTION

1. Field of the Invention

The present invention relates to a method for regulating expression of PDGFC, FGF2, IGF1R, PTGIS, NOS3, EDN1, PLAT, PROC, VWF, F3, SERPINE1, IL-8, ICAM1, VCAM1, and CASP8 genes, comprising administering to a subject in need thereof a composition comprising an effective amount of a plant extract.

2. The Prior Art

The cardiovascular disease is a major threat to human health. According to the information released by the Ministry of Health and Welfare, Taiwan, among the top ten causes of death among Taiwanese, the cardiovascular disease accounts for three, including heart disease and cerebrovascular disease, which rank second and fourth respectively. In the United States, cardiovascular disease is the leading cause of death for the American people. It can be seen that the threat of cardiovascular disease to human health has reached a level that cannot be ignored. At the beginning of the onset, there are usually no obvious symptoms, but when complications occur, such as stroke, myocardial infarction, heart failure, renal failure or retinal hemorrhage, patient's life has often been seriously threatened. In order to treat cardiovascular diseases, the demand for cardiovascular drugs is also high, becoming a huge burden of medical resources. Therefore, those skilled in the art are committed to developing products (including food products and medicaments) for cardiovascular protection in response to the needs of a wide range of human health.

In recent years, the use of plants as raw materials to develop therapeutic medicaments or food products for preventive health care has gradually gained market attention. For example, certain plants are often used to make food or drink ingredients, including tea or grapes. However, those skilled in the art do not currently combine the aforementioned plant extracts and develop medicaments or food products. If it is a certain plant extract, it must be administered at a relatively high dose, which has its limitations in terms of cost of use and effect. Therefore, if a small amount of components of various extracts can be administered, a high dose effect of a single component can be produced, which will bring about a considerable breakthrough in the art.

SUMMARY OF THE INVENTION

A primary objective of the present invention is to provide a method for regulating expression of PDGFC, FGF2, IGF1R, PTGIS, NOS3, EDN1, PLAT, PROC, VWF, F3, SERPINE1, IL-8, ICAM1, VCAM1, and CASP8 genes, comprising administering to a subject in need thereof a composition comprising an effective amount of a plant extract, wherein the plant extract comprises at least one combination selected from the group consisting of a grape seed extract and a Four seasons spring tea extract, a black tea extract and a spinach extract, a grape seed extract and a spinach extract, a grape seed extract and a green coffee bean extract, a red wine extract and a Pu-erh tea extract, and a grape seed extract and a Pu-erh tea extract.

According to an embodiment of the present invention, the plant extract comprises at least 0.0039 mg/mL of the grape seed extract, and at least 0.0039 mg/mL of the Four seasons spring tea extract, at least 0.0039 mg/mL of the spinach extract, at least 0.0039 mg/mL of the green coffee bean extract, or at least 0.0039 mg/mL of the Pu-erh tea extract.

According to an embodiment of the present invention, the plant extract comprises at least 0.0625 mg/mL of the black tea extract and at least 0.0625 mg/mL of the spinach extract.

According to an embodiment of the present invention, the plant extract comprises at least 0.0156 mg/mL of the red wine extract and at least 0.0156 mg/mL of the Pu-erh tea extract.

According to an embodiment of the present invention, the composition provides a cardiovascular protective effect.

According to an embodiment of the present invention, the composition further comprises a pharmaceutically acceptable carrier.

According to an embodiment of the present invention, the composition is in a form of powder, granule, liquid, gel or paste.

According to an embodiment of the present invention, the composition is prepared in a form of a medicament or a food product.

In summary, the composition comprising at least one combination selected from the group consisting of a grape seed extract and a Four seasons spring tea extract, a black tea extract and a spinach extract, a grape seed extract and a spinach extract, a grape seed extract and a green coffee bean extract, a red wine extract and a Pu-erh tea extract, and a grape seed extract and a Pu-erh tea extract providing the effect on cardiovascular protection through regulating expression of cardiovascular-related genes, including PDGFC, FGF2, IGF1R, PTGIS, NOS3, EDN1, PLAT, PROC, VWF, F3, SERPINE1, IL-8, ICAM1, VCAM1 and CASP8.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

FIG. 1 is a histogram showing the effect of a combination of the plant extract on the regulation of cardiovascular-related gene expression in an embodiment of the invention.

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

As used herein, the term "gene" refers to a DNA sequence, including but not limited to: DNA sequences transcribed into mRNA (which can be translated into polypeptide chains), transcribed into rRNA or tRNA, or for enzymes and other proteins involved in DNA replication, transcription, and regulation as recognition sites. This definition includes a variety of sequence polymorphisms, mutations, and/or sequence variants, wherein such alternation does not affect the function of the gene product. The term "gene" is intended to include regions that encode not only gene products but also regulatory regions including, for example, promoters, termination regions, translational regulatory sequences (such as ribosome-binding sites and internal ribosome entry sites), enhancers, silencers, insulators, boundary elements, replication origins, matrix attachment sites, and locus control regions. The term "gene" further includes all introns and other DNA sequences spliced from mRNA transcripts, as well as variants resulting from alternative splice sites.

As used herein, the term "cardiovascular protection" means capable of treating a cardiovascular disease, protecting the cardiovascular system, or reducing the risk of cardiovascular diseases.

According to the present invention, the medicament can be manufactured to a dosage form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The medicament according to the present invention may be administered by a parenteral route selected from the group consisting of: intraperitoneal injection, subcutaneous injection, intramuscular injection and intravenous injection.

According to the present invention, the medicament may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, disintegrating agent, dispersing agent, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

According to the present invention, the composition can be used as a food additive, added by the conventional method in the preparation of the raw material, or added during the preparation of food, and prepared with any edible material into food products for human and non-human animals.

According to the present invention, types of food products include, but not limited to, beverages, fermented foods, bakery products, health foods, and dietary supplements.

Example 1

Source or Preparation of Various Plant Extracts

The grape seed extract of the examples of the present invention is obtained by extracting the seed of *Vitis* spp., and the extract can be purchased from Guarante Biotech Co., Ltd. The Pu-erh tea extract is obtained by extracting post-fermented leaves of *Camellia sinensis*, which can be purchased from Nanjing Zelang Biotechnology Co., Ltd. The spinach extract is obtained by extracting *Spinacia oleracea*, which can be purchased from HONHSIANG FARM PRODUCTS FACTORY. The red wine extract is obtained by extracting red wine, which can be purchased from Shanghai Boyoutang Biotechnology Co., Ltd. The green coffee bean extract is obtained by extracting seeds of unroasted *Coffea* spp., and the extract is commercially available from ARJUNA NATURAL EXTRACTS Co., Ltd. (India).

This example illustrates the preparation process of the extract of the black tea leaves (*Camellia sinensis* leaves) of the present invention. First, the black tea leaves were washed and dried, and were coarsely crushed by a pulverizer. Next, the obtained crude black tea was extracted by using water as a solvent, and the solvent and the crude black tea were uniformly mixed at a liquid-solid ratio of 5-20:1-5. The extraction temperature is 50° C.-100° C., preferably 75° C.-95° C. In this example, the extraction time is 0.5 to 3 hours.

After the black tea extract obtained by the above extraction step was cooled to room temperature, it was filtered through a strainer of 400 mesh to remove residual solids. The filtered black tea extract can be further concentrated under reduced pressure at 45° C. to 70° C. to obtain a concentrated product.

This example illustrates the preparation process of the Four seasons spring tea extract of the present invention. First, the Four seasons spring tea leaves were washed and dried, and were coarsely crushed by a pulverizer. Next, the obtained crude Four seasons spring tea was extracted by using water as a solvent, and the solvent and the crude Four seasons spring tea were uniformly mixed at a liquid-solid ratio of 5-20:1-5. The extraction temperature is 50° C.-100° C., preferably 75° C.-95° C. In this example, the extraction time is 0.5 to 3 hours.

After the Four seasons spring tea extract obtained by the above extraction step was cooled to room temperature, it was filtered through a strainer of 400 mesh to remove residual solids. The filtered Four seasons spring tea extract can be further concentrated under reduced pressure at 45° C. to 70° C. to obtain a concentrated product.

Example 2

Effect of Combination of Plant Extracts on Regulating Cardiovascular-Related Gene Expression First, human umbilical vein endothelial cells (HUVEC; purchased from the Biosource Collection and Research Center (BCRC), Food Industry Research and Development Institute (FIRDI), Taiwan, BCRC number: H-UV001) were cultured in the EC medium supplemented with medium 200 (M200) and 10% low serum growth supplement (LSGS)

(Gibco; Cat. No. M-200-500). 2 mL of the EC medium was added to each well of a 6-well culture plate to have $1.5 \times 10^5$ HUVEC cells per well.

The HUVEC cell samples were then divided into 13 groups, of which seven comparative groups (comparative group 1 to comparative group 7) and six experimental groups (i.e., experimental group 1 to experimental group 6) were prepared. An appropriate amount of each plant extract according to Example 1 was added to the cells in each group, the cells in each group were cultured in an incubator, and the medium was changed at 6, 24 hours and the plant extract or the combination of plant extracts was added. The types, concentrations, and/or ratios of the plant extracts added to cells in each group are shown in Table 1.

TABLE 1

| Group | Types and concentrations of plant extracts | Ratios (v/v) |
|---|---|---|
| comparative group 1 | black tea extract (0.0625 mg/mL) | — |
| comparative group 2 | spinach extract (0.0625 mg/mL) | — |
| comparative group 3 | grape seed extract (0.003906 mg/mL) | — |
| comparative group 4 | green coffee bean extract (0.003906 mg/mL) | — |
| comparative group 5 | red wine extract (0.015625 mg/mL) | — |
| comparative group 6 | Pu-erh tea extract (0.015625 mg/mL) | — |
| comparative group 7 | Four seasons spring tea extract (0.003906 mg/mL) | — |
| experimental group 1 | grape seed extract + Four seasons spring tea extract (0.00390625 mg/mL + 0.00390625 mg/mL) | 1:1 |
| experimental group 2 | black tea extract + spinach extract (0.0625 mg/mL + 0.0625 mg/mL) | 1:1 |
| experimental group 3 | grape seed extract + spinach extract (0.00390625 mg/mL + 0.00390625 mg/mL) | 1:1 |
| experimental group 4 | grape seed extract + green coffee bean extract (0.00390625 mg/mL + 0.00390625 mg/mL) | 1:1 |
| experimental group 5 | red wine extract + Pu-erh tea extract (0.015625 mg/mL + 0.015625 mg/mL) | 1:1 |
| experimental group 6 | grape seed extract + Pu-erh tea extract (0.00390625 mg/mL + 0.00390625 mg/mL) | 1:1 |

After culturing in the incubator, cell cultures in each group were collected and subjected to gene expression analysis.

In this example, the target genes for analyzing cardiovascular related genes include the platelet-derived growth factor C (PDGFC) gene, the fibroblast growth factor 2 (FGF2) gene, the insulin-like growth factor 1 receptor (IGF1R) gene, the prostaglandin I2 synthase (PTGIS) gene, the nitric oxide synthase 3 (NOS3) gene, the endothelin 1 (EDN1) gene, the plasminogen activator, tissue (PLAT) gene, the protein C (PROC) gene, the von Willebrand factor (VWF) gene, the F3 gene, the serpin peptidase inhibitor E1 (SERPINE1) gene, the interleukin-8 (IL-8) gene, the intercellular adhesion molecule 1 (ICAM1) gene, the vascular cell adhesion molecule 1 (VCAM1) gene, and the caspase 8 (CASP8) gene.

RNA extraction was performed using an RNA extraction kit (Geneaid). 2,000 ng of the RNA in each group thus obtained was taken and the extracted RNA was reverse transcribed into cDNA by SuperScript® III reverse transcriptase (Invitrogen). The cDNA was used as a template, primer pairs for amplification of target genes, including PTGIS, NOS3, EDN1, PLAT, VWF, F3, SERPINE1, ICAM1, VCAM1, IL-8, CASP8, PDGFC, FGF2, IGF2BP3, IGF1R, and ACTB (as internal control) were used, and their nucleotide sequences are shown in Table 2. The quantification of target genes was measured by quantitative real-time PCR using KAPA SYBR FAST qPCR kit (2×) (KAPA Biosystems) carried out in Step One Plus Real-Time PCR system (ABI). The melting curves of the PCR product were analyzed during the quantitative real-time PCR.

TABLE 2

| Target gene | SEQ ID NO. # | Primer name | Sequence (5'-->3') |
|---|---|---|---|
| PTGIS | SEQ ID NO. 1 | PTGIS-F | GGCAGACGGGCGAGAAT |
|  | SEQ ID NO. 2 | PTGIS-R | CCCCCCAGGGCATGTT |
| NOS3 | SEQ ID NO. 3 | NOS 3-F | GTTCACCTACATCTGCAACCACAT |
|  | SEQ ID NO. 4 | NOS3-R | AATGCAGAGCTCGGTGATCTC |
| EDN1 | SEQ ID NO. 5 | EDN1-F | CACGTTGTTCCGTATGGACTTG |
|  | SEQ ID NO. 6 | EDN1-R | CCTTTCTTATGATTATTCCAGTCTTTCTC |
| PLAT | SEQ ID NO. 7 | PLAT-F | CAGCCTCAGTTTCGCATCAA |
|  | SEQ ID NO. 8 | PLAT-R | CGGTATGTTCTGCCCAAGATC |
| VWF | SEQ ID NO. 9 | VWF-F | TTCAATCACCTTGGTCACATCTTC |
|  | SEQ ID NO. 10 | VWF-R | CGCTGCACAGTCCATTCCT |
| F3 | SEQ ID NO. 11 | F3-F | CGTACTTGGCACGGGTCTTC |
|  | SEQ ID NO. 12 | F3-R | CCTTCTGACTAAAGTCCGTTCATCT |
| SERPINE1 | SEQ ID NO. 13 | SERPINE1-F | GTGGAGAGAGCCAGATTCATCAT |
|  | SEQ ID NO. 14 | SERPINE1-R | CTGCCGTCTGATTTGTGGAA |
| ICAM1 | SEQ ID NO. 15 | ICAM1-F | GGAGCTTCGTGTCCTGTATGG |
|  | SEQ ID NO. 16 | ICAM1-R | AGCCTGGCACATTGGAGTCT |
| VCAM | SEQ ID NO. 17 | VCAM-F | GTTGAAGGATGCGGGAGTATATG |
|  | SEQ ID NO. 18 | VCAM-R | TCATGTTGGCTTTTCTTGCAA |
| IL-8 | SEQ ID NO. 19 | IL8-F | TTTTGCCAAGGAGTGCTAAAGA |
|  | SEQ ID NO. 20 | IL8-R | AACCCTCTGCACCCAGTTTTC |
| CASP8 | SEQ ID NO. 21 | CASP8-F | TCCAAATGCAAACTGGATGA |
|  | SEQ ID NO. 22 | CASP8-R | GGGCACAGACTCTTTTCAGG |
| PDGFC | SEQ ID NO. 23 | PDGFC-F | TAGGGCGCTGGTGTGGTT |
|  | SEQ ID NO. 24 | PDGFC-R | AAGCAGGTCCAGTGGCAAAG |
| FGF2 | SEQ ID NO. 25 | FGF2-F | TGTGCTAACCGTTACCTGGCTAT |
|  | SEQ ID NO. 26 | FGF2-R | TTCTGCCCAGGTCCTGTTTT |

TABLE 2-continued

| Target gene | SEQ ID NO. # | Primer name | Sequence (5'--->3') |
|---|---|---|---|
| IGF2BP3 | SEQ ID NO. 27 | IGF2BP3-F | AGGAGGCAAAACGGTGAATG |
|  | SEQ ID NO. 28 | IGF2BP3-R | CACTTTGCAGAGCCTTCTGTTG |
| IGF1R | SEQ ID NO. 29 | IGF1R-F | GAAAGGAAGCGGAGAGATGTCA |
|  | SEQ ID NO. 30 | IGF1R-R | TCGATGCGGTACAATGTGAAA |
| β-actin | SEQ ID NO. 31 | ACTB-F | CATGTACGTTGCTATCCAGGC |
|  | SEQ ID NO. 32 | ACTB-R | CTCCTTAATGTCACGCACGAT |

The relative expression levels of all target genes were quantified by the SCORE method, and the scores of expressions of cardiovascular-related genes in each group were calculated. The SCORE method was calculated using the cyclic threshold (Ct) value of the ACTB gene (as an internal control group) and the reference gene.

The relative expression of mRNA of the target genes is derived from the equation $2^{-\Delta Ct}$, wherein $\Delta Ct=Ct_{target\ gene}-Ct_{ACTB}$(beta-actin), the difference between the expressions of each of the above genes in the six groups and the blank control group was calculated, and the total of the differences was used as the score of cardiovascular-related gene expression.

The composition of the present invention has been confirmed to have cardiovascular protective effects through regulating cardiovascular-related gene expression, among which genes related to blood vessel growth include the PDGFC gene, the FGF2 gene, and the IGF1R gene; genes related to vascular elasticity include the PTGIS gene, the NOS3 gene, and the EDN1 gene; genes related to thrombosis include the PLAT gene, the PROC gene, the VWF gene, the F3 gene, and the SERPINE1 gene; genes related to inflammatory factors include the IL-8 gene, the ICAM1 gene, and the VCAM1 gene; and genes related to apoptosis include the CASP8 gene.

The results of this example are shown in FIG. 1 and Table 3. FIG. 1 is a histogram showing the effect of a combination of the plant extract on the regulation of cardiovascular-related gene expression in an embodiment of the invention. Table 3 corresponds to the scores of the expressions of the cardiovascular-related genes calculated for each group in FIG. 1. Among them, the higher score represents more cardiovascular protective effects.

TABLE 3

| Group | Scores of expressions of cardiovascular-related genes |
|---|---|
| comparative group 1 | 7.7 |
| comparative group 2 | 9.1 |
| comparative group 3 | 7.3 |
| comparative group 4 | 8.9 |
| comparative group 5 | 18.22 |
| comparative group 6 | 11.44 |
| comparative group 7 | 3.99 |
| experimental group 1 | 16.66 |
| experimental group 2 | 19.5 |
| experimental group 3 | 22.7 |
| experimental group 4 | 16.51 |

TABLE 3-continued

| Group | Scores of expressions of cardiovascular-related genes |
|---|---|
| experimental group 5 | 32.76 |
| experimental group 6 | 25.17 |

As shown in FIG. 1 and Table 3, in comparison with comparative group 3 (i.e., those treated with the grape seed extract) and comparative group 7 (i.e. those treated with the Four seasons spring tea extract), the score calculated from experimental group 1 (i.e., those treated with the combination of the grape seed extract and the Four seasons spring tea extract) was significantly improved, and was higher than the sum of the scores of comparative group 3 and comparative group 7. In comparison with comparative group 1 (i.e., those treated with the black tea extract) and comparative group 2 (i.e. those treated with the spinach extract), the score calculated from experimental group 2 (i.e., those treated with the combination of the black tea extract and the spinach extract) was significantly improved, and was higher than the sum of the scores of comparative group 1 and comparative group 2. In comparison with comparative group 2 and comparative group 3, the score calculated from experimental group 3 (i.e., those treated with the combination of the grape seed extract and the spinach extract) was significantly improved, and was higher than the sum of the scores of comparative group 2 and comparative group 3. In comparison with comparative group 3 and comparative group 4 (i.e., those treated with the green coffee bean extract), the score calculated from experimental group 4 (i.e., those treated with the combination of the grape seed extract and the green coffee bean extract) was significantly improved, and was higher than the sum of the scores of comparative group 3 and comparative group 4. In comparison with comparative group 5 (i.e., those treated with the red wine extract) and comparative group 6 (i.e., those treated with the Pu-erh tea extract), the score calculated from experimental group 5 (i.e., those treated with the combination of the red wine extract and the Pu-erh tea extract) was significantly improved, and was higher than the sum of the scores of comparative group 5 and comparative group 6; and in comparison with comparative group 3 and comparative group 6, the score calculated from experimental group 6 (i.e., those treated with the combination of the grape seed extract and the Pu-erh tea extract) was significantly improved, and was higher than the sum of the scores of comparative group 3 and comparative group 6.

Therefore, the experimental results of the examples of the present invention show that the combination of various plant extracts of the present invention has the effect on regulating expressions of cardiovascular-related genes. Accordingly, the composition of the present invention has cardiovascular protective effect through regulating expressions of cardiovascular-related genes, including PDGFC, FGE2, IGF1R, PTGIS, NOS3, EDN1, PLAT, PROC, VWF, F3, SERPINE1, IL-8, ICAM1, VCAM1 and CASP8. Further, the composition of the present invention can also be prepared in the form of a medicament or a food product without limitation.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method of treating thrombosis in a human in need thereof consisting essentially of administering to the human in need thereof therapeutically effective amounts of an extract selected from the group consisting of Pu-erh extract and four seasons spring tea extract and an extract selected from the group consisting of spinach extract, black tea extract, grape seed extract, and red wine extract to effectively treat the thrombosis in the human in need thereof.

2. The method of claim 1, wherein the therapeutically effective amounts of the grape seed extract, the Four seasons spring tea extract, the spinach extract and the Pu-erh tea extract are at least 0.0039 mg/mL.

3. The method of claim 1, wherein the therapeutically effective amounts of the black tea extract and the spinach extract are at least 0.0625 mg/mL.

4. The method of claim 1, wherein the therapeutically effective amounts of the red wine extract and the Pu-erh tea extract are at least 0.0156 mg/mL.

* * * * *